US012138523B2

(12) United States Patent
Martin-Niedecken

(10) Patent No.: US 12,138,523 B2
(45) Date of Patent: Nov. 12, 2024

(54) TRAINING MODULE

(71) Applicant: Sphery AG, Au SG (CH)

(72) Inventor: Anna Lisa Martin-Niedecken, Küsnacht (CH)

(73) Assignee: Sphery AG, Au SG (CH)

( * ) Notice: Subject to any disclaimer, the term of this patent is extended or adjusted under 35 U.S.C. 154(b) by 826 days.

(21) Appl. No.: 17/286,369

(22) PCT Filed: Oct. 17, 2018

(86) PCT No.: PCT/EP2018/078417
§ 371 (c)(1),
(2) Date: Apr. 16, 2021

(87) PCT Pub. No.: WO2020/078546
PCT Pub. Date: Apr. 23, 2020

(65) Prior Publication Data
US 2021/0339111 A1    Nov. 4, 2021

(51) Int. Cl.
*G09B 19/00* (2006.01)
*A63B 24/00* (2006.01)
*A63B 71/06* (2006.01)

(52) U.S. Cl.
CPC ...... *A63B 71/0622* (2013.01); *A63B 24/0062* (2013.01); *A63B 24/0075* (2013.01); *A63B 2071/063* (2013.01); *A63B 2071/065* (2013.01); *A63B 2214/00* (2020.08); *A63B 2220/51* (2013.01); *A63B 2220/803* (2013.01);
(Continued)

(58) Field of Classification Search
CPC ... G09B 19/003; G09B 19/0038; G03B 21/56
See application file for complete search history.

(56) References Cited

U.S. PATENT DOCUMENTS 5,882,204 A * 3/1999 Lannazo ............ A63B 24/0021
473/422
8,795,138 B1    8/2014 Yeh et al.
(Continued)

FOREIGN PATENT DOCUMENTS

DE    102012101152 A1    8/2013
DE    102017102144 A1    8/2018
(Continued)

OTHER PUBLICATIONS

International Search Report and Written Opinion mailed on Mar. 19, 2019 in PCT Application No. PCT/EP2018/078417, 14 pages.

*Primary Examiner* — Peter R Egloff
(74) *Attorney, Agent, or Firm* — Procopio, Cory, Hargreaves & Savitch LLP

(57) ABSTRACT

The invention relates to an interactive training module, comprising at least one image-displaying wall (1, 2) with which motion sequences and/or objects can be displayed to a user, at least one position sensing device (7) with which the positions of at least the user's hands can be detected, and a control unit with which these positions can be compared with those which are stored in the control unit, wherein the control unit can display correction information to the user by means of the at least one image-displaying wall (1, 2) on the basis of the difference between the stored position and the detected position.

15 Claims, 3 Drawing Sheets

(52) U.S. Cl.
CPC ... *A63B 2220/833* (2013.01); *A63B 2220/836* (2013.01); *A63B 2230/062* (2013.01)

(56) References Cited

U.S. PATENT DOCUMENTS

| | | | |
|---|---|---|---|
| 2006/0114171 A1* | 6/2006 | Vascotto | G09B 9/02 345/1.1 |
| 2009/0233769 A1* | 9/2009 | Pryor | G16H 20/30 482/8 |
| 2012/0075697 A1* | 3/2012 | Astill | G03B 21/58 359/461 |
| 2012/0079555 A1* | 3/2012 | Choi | G09B 19/0015 725/139 |
| 2013/0004928 A1 | 1/2013 | Ackerman | |
| 2013/0171601 A1 | 7/2013 | Yuasa et al. | |
| 2013/0260342 A1* | 10/2013 | Stanley | F41G 3/2655 434/16 |
| 2014/0080638 A1* | 3/2014 | Feng | A63B 24/0006 473/439 |
| 2014/0174174 A1* | 6/2014 | Uehara | A61B 5/227 700/91 |
| 2015/0099252 A1* | 4/2015 | Anderson | G06T 7/251 434/257 |
| 2016/0354636 A1* | 12/2016 | Jang | A61B 5/681 |
| 2017/0151484 A1* | 6/2017 | Reilly | A63B 69/0024 |
| 2019/0250332 A1* | 8/2019 | Cippant | G02B 6/08 |

FOREIGN PATENT DOCUMENTS

| | | |
|---|---|---|
| JP | 2001-042260 A | 2/2001 |
| JP | 2004-012626 A | 1/2004 |
| JP | 2010-175844 A | 8/2010 |

\* cited by examiner

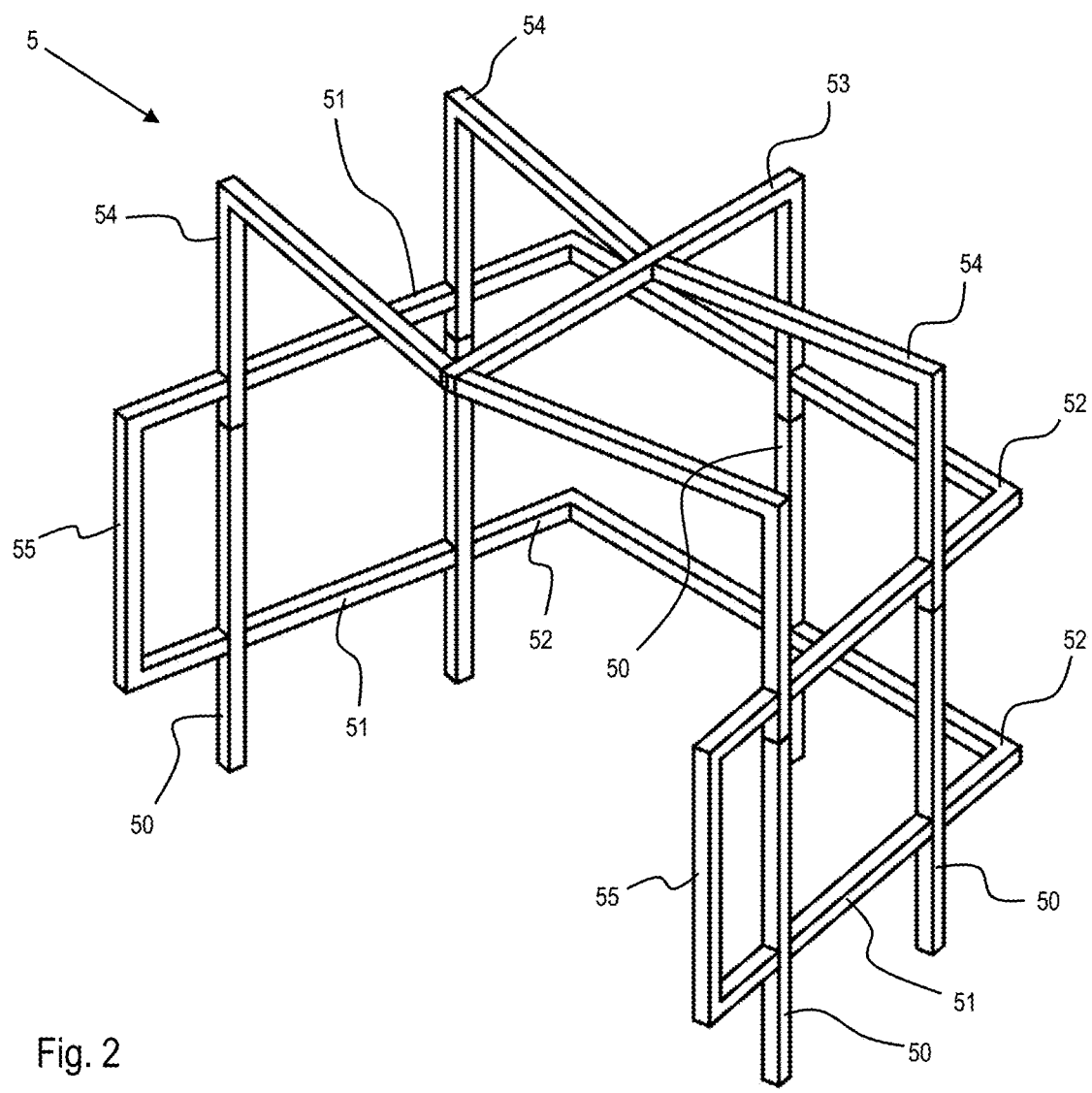
Fig. 2
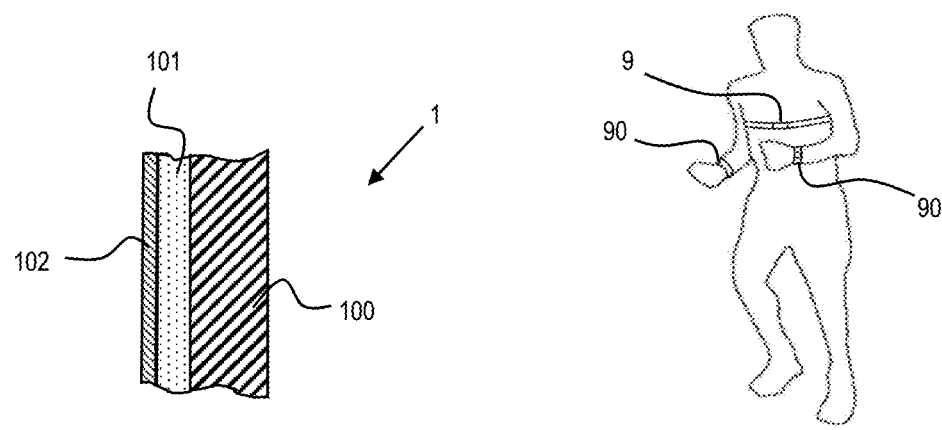
Fig. 3
Fig. 4

TRAINING MODULE

CROSS-REFERENCE TO RELATED APPLICATIONS

This application is a U.S. National Stage entry of PCT Application No: PCT/EP2018/078417 filed Oct. 17, 2018, the contents of which are incorporated herein by reference.

FIELD OF THE INVENTION

The present invention relates to a training module, in particular an interactive training module for the human body.

DESCRIPTION OF THE PRIOR ART

To train the body, many people go to a gym, where they can perform exercises supervised by an instructor. The exercises can be performed in group classes or individual classes, which take place at predetermined times. Accordingly, it is not possible to exercise at any time. To increase the flexibility and individuality of the training, instructional videos are offered. These can be played independently on a screen at home, for example. The exercises are displayed on the screen and instructions are given over the loudspeakers. A user of such an instructional video has no way of knowing whether he or she is performing the exercises, or instructions, correctly. It is also the case that an exercise must be selected in advance and then it runs automatically, regardless of the exercise being performed by the user. If the selected exercise does not correspond to the user's performance level, the user must manually select another exercise.

DESCRIPTION OF THE INVENTION

One object of the present invention is to provide a training module that allows independent training without a physical instructor, with a high quality of training adapted to the user.

This object is solved by a training module with the features of claim 1. Further embodiments of the training module, a training system, and a method for operating a training module are defined by the features of further claims.

An interactive training module according to the invention comprises at least one image-displaying wall with which motion sequences and/or objects can be displayed to a user, at least one position sensing device with which the positions of at least the hands of the user can be detected, and a control unit with which these positions can be compared with those which are stored in the control unit, wherein the control unit can display correction information to the user by means of the at least one image-displaying wall on the basis of the difference between the stored position and the detected position.

Such a training module allows independent training with an optimal training effect. By continuously detecting the position of at least the hands, their movement can be determined by means of the control unit. The position detection or the movement detection can also take place in intervals, the time intervals of which can be set; for example, short time intervals for fast exercises and longer time intervals for slower exercises.

The movement sequences can be sequences for only individual limbs or can affect the entire body. For example, individual exercises such as push-ups, squats or the like can be displayed, or several sequences to be performed in succession can be displayed, such as in yoga, tai chi or the like. Such a training module can cover a wide range of requirements, for example in the field of rehabilitation and/or elderly care.

The training module offers the possibility of predefining player types, which differ, for example, in their physical and mental capabilities. The user can select a player type and the system compares the defaults with the movements performed by the user. Alternatively, the system may require the user to complete a tutorial that allows the system to assign a player type. This can be carried out before each training session to verify current performance.

Alternatively, this may be carried out only for the first time, or the system may require the user to do this if their last workout was a long time ago. The system can suggest a different player type if it is detected that the movements performed by the user deviate too much from the defaults. The training module therefore offers a demand and promotion optimally adapted to the user and thus balanced and maximally effective training is guaranteed. The adaptation to the individual needs can be carried out in real time.

Alternatively or additionally, movement instructions can be displayed in the form of objects that indicate to the user in which direction he should move which limbs. For example, a route can be displayed which the user should follow. By moving the limbs, the user can indicate or change his direction of movement. The route may include obstacles that prompt the user to dodge, jump up, or duck. A visual feedback on the wall can show the user how well he has followed the given route.

In one embodiment, the position sensing device comprises at least one camera, with which the area in front of the wall can be detected, whereby the movements of a user in front of the wall can be detected. All joints on the body are tracked with a camera or a comparable technology, i.e. their movement is recorded and evaluated. This enables a very accurate comparison of the training instruction with the actual movement performed, which allows a qualitatively high level of feedback regarding the execution of the movement. This information can also be used to instruct the improvement of the movements at the next attempt. Accordingly, the training can be optimized and injuries, for example due to overload, can be avoided.

The user can wear special clothing or can wear markings that improve the detection of movements by means of the camera. Alternatively or additionally, the position sensing device comprises at least one inductive, capacitive or infrared light detecting sensor with which the area in front of the wall can be detected. For example, the sensor can detect the light of an infrared laser.

In one embodiment, the interactive training module comprises at least one speaker with which instructions can be given. For example, the exercise to be completed can be explained. Alternatively or additionally, acoustic correction instructions can be given. For example, the user may be prompted to react faster or move more accurately. Alternatively or additionally, motivational or animating comments or music may be provided. For example, the user may be prompted to persevere a little longer or music may be played that matches the intensity of the exercise being completed. The speakers can also be used to communicate with other users. In this case, the training module also includes at least one microphone.

In one embodiment, the interactive training module comprises at least one heart rhythm sensor with which the user's heart rhythm can be detected continuously and/or at intervals. For example, the resting heart rate can be detected before the exercise begins. The training module then suggests an exercise that is matched to the detected resting pulse. Further information can be recorded before the start of the exercise, which can then be used by the training module for optimum exercise selection or optimum suggestion of an exercise. For example, age, weight and general fitness can be entered. In addition, preferences can be specified regarding the visual representation of the exercises on the wall. For example, a technical representation or a natural representation can be selected.

In one embodiment, the control unit uses the sensed heart rhythm to adjust the difficulty and/or intensity of the exercise program. The adjustment may occur during the exercise, or it may occur afterward. For example, the adjustment may be made in real time and without the intervention of an instructor or trainer, thereby always keeping the user in their optimal exercise state. For example, if it is determined during an exercise that the user's heart rhythm, or pulse, is very high, the speed at which the predetermined movements are to be performed may be reduced, or the intensity of the movements may be reduced. For example, the intensity of the exercise can be reduced, i.e. the size of the movements can be reduced. Alternatively or additionally, the time intervals between the exercises to be completed can be increased. Conversely, the movements can be increased and the time intervals can be decreased if the exercises are to be intensified.

In one embodiment, the interactive training module comprises a force sensor integrated into the at least one image-displaying wall. The wall may also comprise several integrated force sensors, which are arranged evenly or randomly distributed over the surface. By means of the force sensors, the control unit can detect the location and intensity of a contact with the wall. Based on the evaluation of the recorded data, the control unit can indicate to the user on the wall whether his touches were too inaccurate, too strong or too weak, or occurred at an incorrect time.

In one embodiment, the at least one image-displaying wall is a screen.

In one embodiment, the interactive training module comprises at least one projector with which an image can be displayed on the image-displaying wall. A displayed image may cover a portion, portions, or the entire wall. For example, projection of a 150 inch image at a distance of 50 centimeters is possible with an ultra-short distance laser projector. Such projectors are characterized by a very high contrast value. Thus, a high-quality image can be projected even in low light conditions.

In one embodiment, the at least one image-displaying wall comprises a supporting first layer and a haptic second layer, wherein the haptic layer is disposed on the side of the supporting layer facing the user.

In one embodiment, the first layer comprises an MDF board and the second layer comprises a foam board, a silicone board, or a silicone foam board that is glued to the MDF board.

In one embodiment, the at least one image-displaying wall comprises an optical third layer, wherein the optical layer is disposed on the side of the haptic layer facing the user.

In one embodiment, the third layer comprises a canvas stretched over at least the foam or silicone sheet.

In one embodiment, the interactive training module comprises a first wall and at least one second wall laterally adjacent to the first wall in the intended use position, wherein the at least one second wall is oriented at an angle to the first wall.

In one embodiment, the first wall and the at least one second wall enclose an angle of 90 degrees or more on the side facing the user. For example, an angle of 110 degrees. The second wall may be connected in an articulated manner to the first wall, allowing the angle spanned by the two walls to be adjustable. Alternatively, however, the angle may be less than 90 degrees.

In one embodiment, the interactive training module includes a first wall and two second walls that connect laterally to the first wall on either side thereof. Additional walls may be provided, for example, a total of four, five, six or more walls may be provided, which together form an open area or a closed area. In the case of a closed area, a door may be provided or one of the walls may be pivotable or slidable. In addition to the side walls, a ceiling may be provided, which may also serve as an image-displaying wall and may also include integrated force sensors. Alternatively, the open areas of the training module can be closed with a curtain or a rouleau. This applies to the side, i.e. the walls, as well as to the ceiling.

In one embodiment, the walls comprise at least one panel and a portion of a corner piece connecting the first wall to the second wall in a substantially seamless manner. The corner piece may also be sharp-edged. Likewise, it is conceivable that a wall comprises a plurality of panels which are butt-joined. In an alternative embodiment without a corner piece, two adjacent panels can be arranged adjoining one another at an angle. It is also possible to join two adjacent panels together in an articulated manner, whereby the panels can be arranged at any angle to each other. The panels of a wall can also be arranged on rails at least partially offset from one another, whereby the width of the wall can be easily adjusted. Likewise, one or both side walls may be designed to be movable, whereby the space between the walls can be easily changed. A panel can comprise one or more plates, which are arranged vertically and/or horizontally next to or above each other.

In one embodiment, the interactive training module comprises two or more projectors, wherein an image can be displayed on each of the walls with at least one of the projectors. Single or multiple partial images may also be displayed. Alternatively or additionally, a projector may display an image on two walls adjacent to each other.

In one embodiment, the interactive training module comprises a framework on which at least the walls are arranged. The framework can be arranged free-standing in the room or can be firmly connected to the floor, the walls or the ceiling.

In one embodiment, the framework projects upwards above the walls in the intended use position and the projectors and/or the position sensing device are arranged on the part of the framework projecting above the walls. The projectors may be arranged directly on the framework or they may be arranged on the framework with a mounting, for example a retaining plate. The retaining plate may be attached to one or more beams of the framework. Alternatively, the projectors and/or position sensing device may be arranged on a ceiling located above the training module. Likewise, it is possible to integrate the projectors and/or position sensing devices into the walls. If the projectors are integrated into the walls, then corresponding recesses are to be provided in the walls through which an image can be projected.

In one embodiment, the parts of the framework that project above the walls are connected to each other. The connection can be made partially or completely via profiles. For example, the profile parts may be connected to each other by a ceiling segment. For example, a wall may be a unit comprising a framework one or more panels, one or more projectors, and one or more position sensing devices. The projectors and position sensing devices may be preset to the corresponding wall. A plurality of such units may then be aligned and interconnected. The number of walls, their position in relation to each other, i.e. their order and their orientation can be entered in the system control unit, which allows for easy and versatile installation.

In one embodiment, the interactive training module comprises a floor, which can be designed to display images and/or which is equipped with force sensors. The force sensors can be evenly or randomly distributed over the floor surface.

In one embodiment, the interactive training module includes at least one projector capable of displaying an image on the floor. Two or more projectors can also be provided, which can project an image onto the floor. Alternatively or additionally, these projectors can also project images or partial images onto the walls. The floor can serve as an interactive input element. It also serves as an orientation aid for the temporally, correct execution of the requested movements. The orientation aid is achieved with the help of audio-visual effects, which display the requested movement on the floor in real time. The floor can also show the starting position, which can vary depending on the size, mental and physical condition of each user.

The mentioned embodiments of the training module can be used in any combination, provided that they do not contradict each other.

An interactive training system according to the invention comprises a training module according to one of the preceding embodiments and at least one tracker which is wearable by a user and with which at least the position of a hand of the user can be detected. Such a tracker may, for example, transmit or receive an infrared signal.

In one embodiment, the interactive training system includes two or more trackers that can be held with the hands or that can be arranged on the user's body with attachment means.

In one embodiment, the attachment means are configured to attach the trackers to at least one of the group of body sites that includes wrist, elbow, shoulder, neck, head, hip, knee, and ankle.

In one embodiment, the training system is designed in such a way that the movements of two or more users can be detected. For this purpose, a corresponding number of position sensing devices is provided in the system and the control unit is designed accordingly. The following embodiments can also be implemented by providing the required number of position sensing devices and the corresponding programming or design of the control unit.

In one embodiment, the recording can take place simultaneously. Alternatively, the recording can be time-delayed. In the time-shifted variant, a user can compete against himself or he can compete against the recorded exercise of another. The system then compares the two users with each other and with the default. Accordingly, the users can perform an exercise together or they can compete against each other. It is possible that when users of different strength classes compete against each other, the stronger player receives a handicap or the weaker player receives an advantage.

In one embodiment, simultaneous detection of multiple users can be performed in one training module and/or in multiple training modules. Thus, two users can act together in one training module or they can each perform their exercise in separate training modules. The different training modules may be located in the same room, in the same building, or in completely different locations. The training modules may be connected to each other in a network, for example, they may be connected to each other via the Internet. Accordingly, it is possible for users from different continents to perform exercises with each other or compete against each other.

The mentioned embodiments of the training system can be used in any combination, provided that they do not contradict each other.

A method of operating a training module according to the invention comprises the following steps:
Providing a training module according to one of the preceding embodiments;
Selecting an exercise by a user;
Starting the exercise by the control unit;
Detecting at least the position of the user's hands by means of the at least one position sensing device;
Compare the detected position with the position stored in the control unit;
Display correction information on the image-displaying wall based on the difference between the stored position and the detected position.

In one embodiment, the method for operating a training module comprises at least one of the steps:
Adjusting the exercise based on the evaluation of the difference between the stored positions and the corresponding detected positions over a specified period of time;
Adjusting the exercise based on the measured heart rhythm over a given period of time.

BRIEF DESCRIPTION OF THE FIGURES

Exemplary embodiments of the present invention are explained in further detail below with reference to figures. These are for explanatory purposes only and are not to be construed restrictively. The figures show as follows:
FIG. 2 shows a perspective view of the framework of FIG. 1;
FIG. 3 shows a partial sectional view through the structure of a wall of FIG. 1;
FIG. 4 shows a user wearing a heart rhythm sensor and wearable trackers.

DETAILED DESCRIPTION OF THE INVENTION

Figure 1:
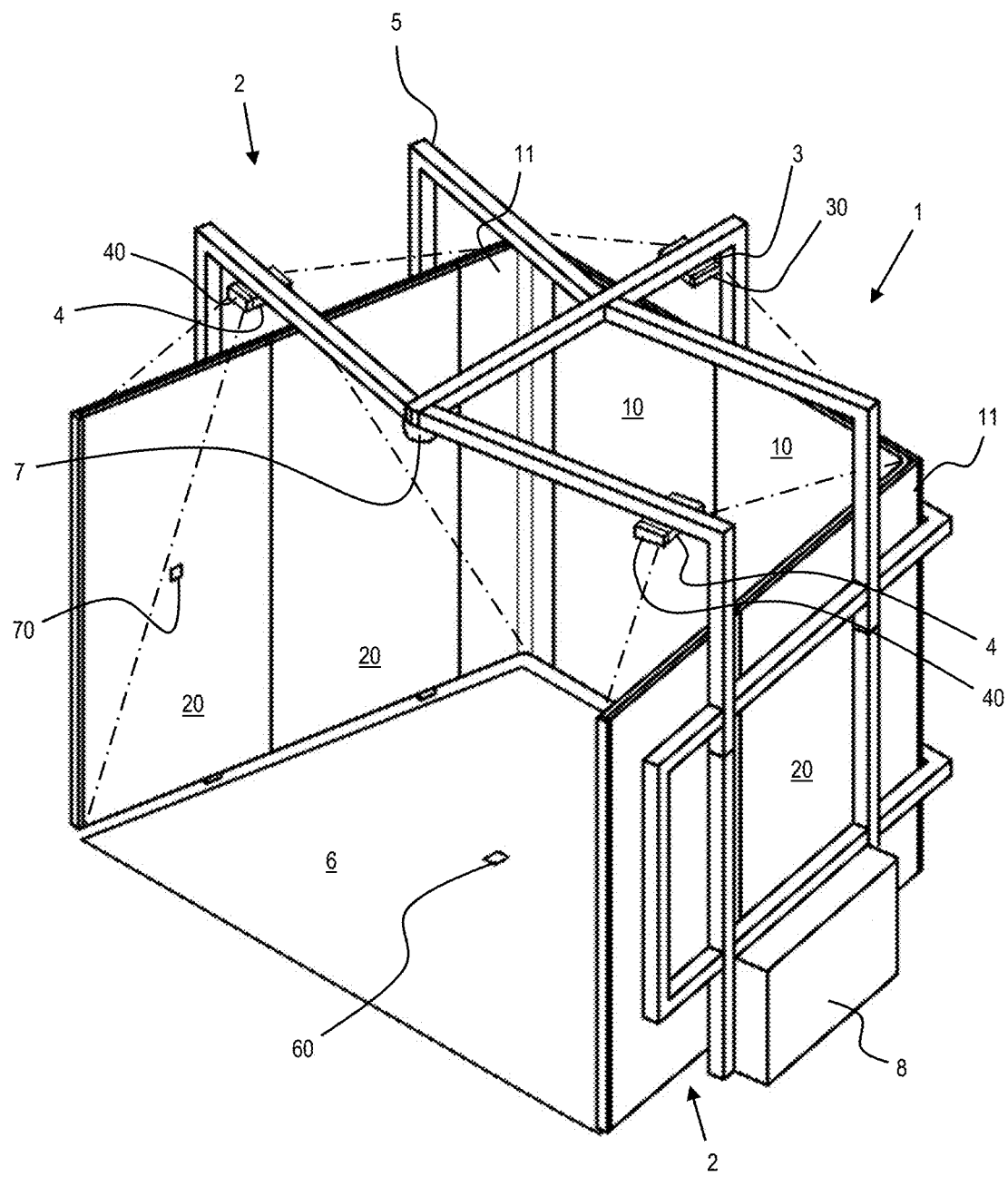
FIG. 1 shows a perspective view of an interactive training module according to the invention.

FIG. 1 shows a perspective view of an interactive training module according to the invention. The training module comprises an image-displaying first wall 1 and two image-displaying second walls 2 arranged laterally adjacent thereto, which are arranged on a framework 5. The second walls 2 are arranged at an angle of more than 90 degrees with respect to the first wall 1. In the embodiment shown, the angle included between the two walls 1, 2 is about 100 degrees. The first wall 1 comprises two panels 10 and each of the second walls 2 comprises two panels 20 which are butt-joined. Between the first wall 1 and the second walls 2, corner pieces 11 are arranged which are butt-joined to the first wall 1 on their one side and which are butt-joined to the second walls 2 on their second side. The corner pieces are rounded, resulting in a substantially stepless transition from the first wall 1 to the second walls 2. Force sensors 70 are arranged on the first and second walls 1, 2. For illustrative purposes, only one force sensor 70 is shown. However, multiple force sensors may be provided distributed across the panels 10, 20 of the walls 1, 2. A floor 6 is provided between the walls 1, 2, which may also be equipped with force sensors 60. Again, only one force sensor 60 is shown for illustrative purposes. The framework 5 comprises several profiles, as shown in detail in FIG. 2. The vertical profiles 50 project above the walls 1, 2 and are connected to each other by ceiling profiles 53, 54. The projectors 3,4 and the position or movement detection devices 7 are arranged on the ceiling profiles 53, 54. For illustration purposes, only one motion sensor 7 is arranged. There is a control unit or a processor of a computer 8, with which the positions detected by the motion sensor 7 can be compared with those which are stored in the control unit 8, wherein the control unit 8 can display correction information to the user by means of the image-displaying walls 1, 2 based on the difference between the stored positions and the detected positions. The visual correction information on the image-displaying walls 1, 2 can be accompanied by acoustic correction information through loudspeakers 30, 40.

FIG. 2 shows a perspective view of the framework 5 of FIG. 1. The framework 5 comprises five vertical profiles 50, wherein the central vertical profile 50 is assigned to the first wall 1 and wherein two lateral vertical profiles 50 are assigned to each of the second walls 2. On the vertical profile 50, which is assigned to the first wall 1, a first ceiling profile 53 is arranged, which extends away from the first wall 1 essentially horizontally between the two second walls 2. A second ceiling profile 54 is arranged at the respective upper end of the vertical profiles 50 associated with the second walls 2 and extends away from the respective second wall 2 essentially horizontally to the first ceiling profile 53. The vertical profiles 50 of the second walls 2 are connected to each other by first horizontal profiles 51, and the second ceiling profiles 54 are also connected to each other by first horizontal profiles 51. At the free end of the second walls 2, the vertical profile 50 and the second ceiling profile 54 are connected to each other by a U-shaped connecting profile 55, wherein the legs of the connecting profile 55 are aligned with the first horizontal profiles 51. On the side of each second wall 2 facing the first wall 1, the vertical profiles 50 are connected to one another by angled second horizontal profiles 52, and the first ceiling profile 53 is connected on both sides to the second ceiling profiles 54 likewise by the angled second horizontal profiles 52. One leg of each of the second horizontal profiles 52 is aligned with each of the second horizontal profiles 51.

FIG. 3 shows a partial sectional view through the structure of a wall 1, 2 of FIG. 1. Each of the panels 10, 20 and each corner profile 11 has the same layered structure. The layered structure comprises a first layer 100 in the form of an MDF board, a second layer 101 in the form of a foam board arranged thereon, and a third layer 102 in the form of a canvas arranged thereon. The foam board 101 is glued to the MDF board and the canvas is stretched over the foam board and the MDF board.

FIG. 4 shows a user wearing a heart rhythm sensor 9 and wearable trackers 90.

Figure 5:
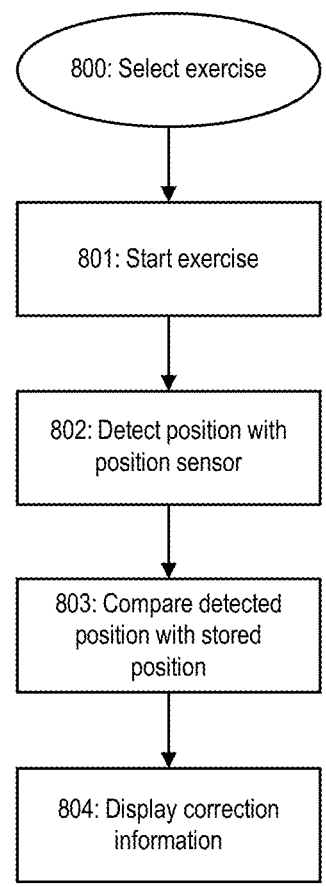
FIG. 5 shows a flow chart of a method for operating the training module according to the invention.

FIG. 5 shows a flow chart of a method for operating the training module according to an exemplary aspect of the present invention. The method includes:
Providing a training module according to one of the preceding embodiments;
Selecting an exercise by a user 800;
Starting the exercise by the control unit 801;
Detecting at least the position of the user's hands by means of the at least one position sensing device 802;
Comparing the detected position with the position stored in the control unit 803;
Displaying correction information on the image-displaying walls 1, 2 based on the difference between the stored position and the detected position 804.

LIST OF REFERENCE NUMERALS

| 1 First wall | 51 First horizontal profile |
|---|---|
| 10 Panel | 52 Second horizontal profile |
| 11 Corner piece | 53 First ceiling profile |
| 100 First layer | 54 Second ceiling profile |
| 101 Second layer | 55 Connecting profile |
| 102 Third layer | 6 Floor |
| 2 Second wall | 60 Force sensor |
| 20 Panel | 7 Motion sensor |
| 3 First projector | 70 Force sensor |
| 4 Second projector | 30 Loudspeaker |
| 5 Framework | 40 Loudspeaker |
| 50 Vertical profile | 9 Heart rhythm sensor |
| 8 Control unit | |
| 90 Wearable tracker | |

The invention claimed is:

1. An interactive training module comprising:
one image-displaying first wall (1);
two image-displaying second walls (2) laterally connected to the first wall (1) on both sides thereof,
three projectors (3,4),
wherein each of the image-displaying walls (1, 2) is configured to display motion sequences and/or objects to a user with one of the three projectors (3,4), at least one position sensor (7) is configured to detect positions of at least the user's hands; and
a processor of a computer configured to compare the positions with those which are stored in the processor,
wherein the processor is configured to display correction information to the user by the image-displaying wall (1) on a basis of a difference between the stored position and the detected position,
wherein the first wall (1) and the two second walls (2), on the side facing the user, include an angle of 90 degrees or more,
wherein the image-displaying walls (1,2) are arranged on a framework (5), which framework (5), in an intended use position, projects upwardly above the walls (1, 2),
wherein the three projectors (3, 4) are arranged on a part of the framework (5) projecting above the walls (1, 2), and
wherein the parts of the framework (5) that project above the image-displaying walls (1,2) are connected to each other.

2. The interactive training module according to claim 1, wherein the position sensor (7) comprises at least one sensor of the group consisting of camera, inductive sensor, capacitive sensor, and infrared light detecting sensor, and is configured to detect an area in front of the wall (1, 2).

3. The interactive training module according to claim 1, further comprising at least one loudspeaker configured to give instructions and/or make acoustic correction indications and/or provide motivating or animating comments or music.

4. The interactive training module according to claim 1, further comprising at least one heart rhythm sensor configured to detect heart rhythm of the user continuously and/or at intervals,
  wherein the processor is further configured to use sensed heart rhythm to adjust a difficulty and/or intensity of a training program.

5. The interactive training module according to claim 1, further comprising a force sensor (70) integrated in the image-displaying first wall (1) and in the image-displaying second walls (2).

6. The interactive training module according to claim 1, wherein the image-displaying first wall (1) and in the image-displaying second walls (2) comprises a supporting first layer (100), a haptic second layer (101) arranged on the side of the first layer (100) facing the user, and an optical third layer (102) arranged on the side of the second layer (101) facing the user.

7. The interactive training module according to claim 6, wherein the first layer (100) comprises an MDF board and wherein the second layer (101) comprises a foam board, a silicone board or a silicone foam board glued to the MDF board (100).

8. The interactive training module according to claim 7, wherein the third layer (102) comprises a canvas stretched over at least the foam board, the silicone board or the silicone foam board (101).

9. The interactive training module according to claim 1, wherein the position sensor (7) is arranged on the part of the framework (5) projecting above the walls (1, 2).

10. The interactive training module according to claim 1, further comprising a floor (6) which is configured to be image-displaying and/or which is equipped with force sensors (60) and comprising at least one projector configured to display an image on the floor (6).

11. An interactive training system, comprising a training module according to claim 1 and at least one tracker which is wearable by a user and configured to detect at least a position of a hand of the user.

12. The interactive training system according to claim 11, wherein the training system is configured to detect movements of two or more users are detectable.

13. The interactive training system of claim 12, wherein the detection is configured to be simultaneous.

14. The interactive training system according to claim 13, wherein simultaneous detection of multiple users is configured to be performed in one training module and/or in multiple training modules.

15. A method for operating a training module comprising:
  providing a training module according to claim 1;
  selecting an exercise by a user;
  starting the exercise by the processor;
  detecting at least the position of the user's hands by the at least one position sensor (7);
  comparing the detected position with the position stored in the processor; and
  displaying correction information on the image-displaying wall (1, 2) based on a difference between a deposited position and the detected position.

* * * * *